(12) United States Patent
Glaser-Seidnitzer et al.

(10) Patent No.: US 7,885,828 B2
(45) Date of Patent: Feb. 8, 2011

(54) KNOWLEDGE-BASED ORDERING SYSTEMING FOR RADIOLOGICAL PROCEDURES

(75) Inventors: Karlheinz Glaser-Seidnitzer, Fürth (DE); Mike Müller, Möhrendorf (DE); Klaus Mayer, Eckental (DE)

(73) Assignee: Siemens Aktiengesellschaft (DE)

( * ) Notice: Subject to any disclaimer, the term of this patent is extended or adjusted under 35 U.S.C. 154(b) by 602 days.

(21) Appl. No.: 11/654,415

(22) Filed: Jan. 17, 2007

(65) Prior Publication Data

US 2008/0172249 A1 Jul. 17, 2008

(51) Int. Cl.
*G06Q 10/00* (2006.01)
(52) U.S. Cl. .............................. 705/3; 600/300; 600/437
(58) Field of Classification Search .................. 705/2–3; 600/300, 437
See application file for complete search history.

(56) References Cited

U.S. PATENT DOCUMENTS 6,394,649 B1 * 5/2002 Moore et al. ................. 378/182
2004/0147840 A1 * 7/2004 Duggirala et al. ........... 600/437
2007/0143136 A1 * 6/2007 Moore et al. .................... 705/2

* cited by examiner

*Primary Examiner*—Gerald J. O'Connor
*Assistant Examiner*—Sind Phongsvirajati
(74) *Attorney, Agent, or Firm*—Brinks Hofer Gilson & Lione

(57) ABSTRACT

A system and method may generate a radiological request by which to conduct a radiological procedure that employs a series of procedural steps to acquire internal images of a patient. Each step may have a corresponding protocol item which affects image quality and the time required to complete the step. A database may be maintained that includes protocol items and patient characteristic data. A rule-based algorithm may accept patient characteristic data as input. Based upon one or more patient characteristics, an overall protocol by which to conduct the radiological procedure may be determined. The tailored protocol may include steps that are selected, omitted, and/or altered based upon a patient characteristic. The patient characteristics may be medical restrictions, such as age, pregnancy, allergies, artificial joints, or other limitations. As a result, the protocol items may be automatically selected based upon patient specific characteristics, and/or an anatomical structure to be examined.

11 Claims, 4 Drawing Sheets

KNOWLEDGE-BASED ORDERING SYSTEMING FOR RADIOLOGICAL PROCEDURES

BACKGROUND

The present embodiments relate generally to medical procedures. In particular, the present embodiments relate to planning radiological procedures.

Conventionally, the manner by which to conduct a radiological procedure may be determined by a Medical Technical Radiological Assistant ("MTRA"). The radiological procedure may be performed by the MTRA or a radiologist. However, inexperienced MTRAs may lack sufficient expertise with respect to one or more types of radiological procedures, impeding the proper selection of protocol items, discussed in further detail below, associated with the procedure.

A radiological procedure to be performed on a particular patient may be initially planned in advance. Before the procedure is actually performed, the patient may be transferred to a different physician or the patient's condition may change. Hence, at the time of the radiological procedure, the treating physician or current MTRA may not have complete and accurate patient information. As a result, the planned procedure by which to conduct a radiological procedure may have shortcomings for various reasons.

BRIEF SUMMARY

By way of introduction, the embodiments described below include methods, processes, apparatuses, instructions, or systems for planning "radiological requests" by which to conduct radiological procedures that acquire internal patient images. A radiological procedure may have a corresponding work list of procedural steps to be performed. Each step may have an associated protocol item that affects the quality of the images acquired and the time required to complete the step. A database may be maintained that stores protocol items and patient characteristic data. A processor may remotely access the database and perform operations upon the data using a rule-based algorithm to select appropriate protocol items based upon the patient characteristics and an anatomical structure to be examined. A suggested overall protocol may be automatically tailored in view of patient limitations and/or restrictions to enhance image quality and reduce the time required to complete the procedure.

In a first aspect, a data processing system recommends a radiological procedure based upon a set of rules. The system includes a processor operable to accept medical information and determine a protocol by which to conduct the radiological procedure by employing a rule-based algorithm that acts upon the medical information.

In a second aspect, a data processing system recommends a radiological procedure based upon a set of rules. The system includes a processor operable to employ a rule-based algorithm to determine a protocol by which to conduct the radiological procedure based upon a patient characteristic and an anatomical structure to be examined.

In a third aspect, a method recommends a radiological procedure based upon a set of rules. The method includes automatically tailoring a protocol by which to conduct the radiological procedure by accounting for a patient characteristic via a processor.

In a fourth aspect, a computer-readable medium having instructions executable on a computer is described. The instructions include employing an algorithm operable to accept a patient characteristic as an input parameter and select a protocol item associated with a step of a radiological procedure based upon the patient characteristic.

The present invention is defined by the claims recited herein. Nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The present embodiments will become more fully understood from the detailed description given herein below and the accompanying drawings which are given by way of illustration only, and are not limitative of the present invention, and wherein.

DETAILED DESCRIPTION OF THE DRAWINGS AND PRESENTLY PREFERRED EMBODIMENTS

Figure 1:
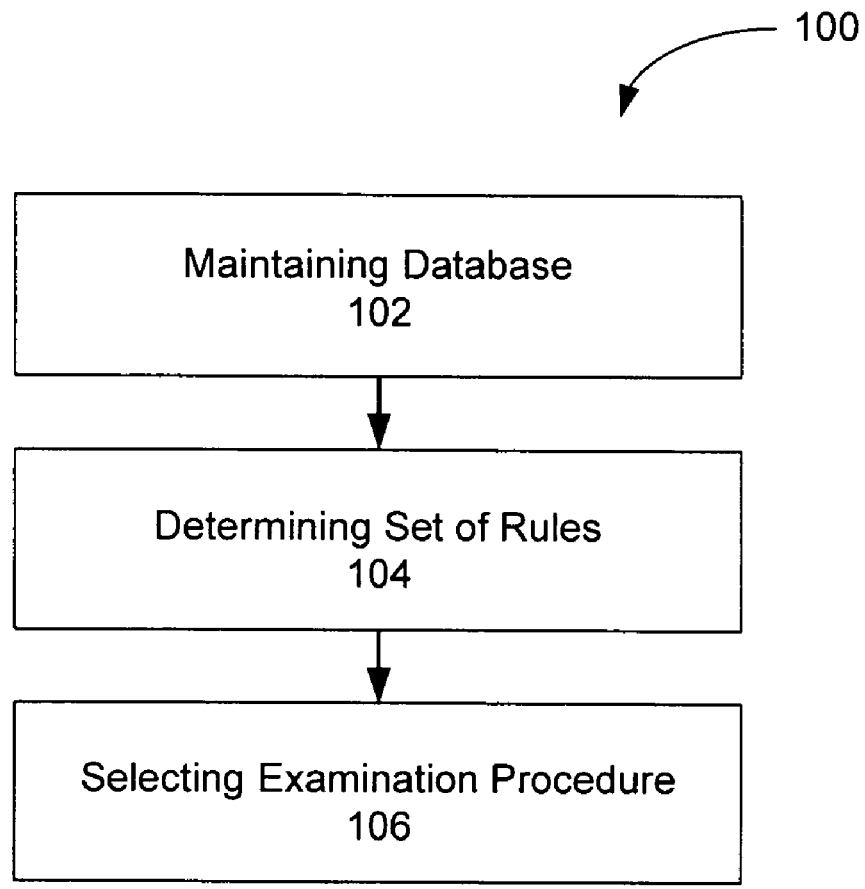
FIG. 1 illustrates an exemplary method of planning a radiological procedure.

The embodiments described herein include methods, processes, apparatuses, instructions, or systems for planning a radiological procedure that acquires internal images of a patient. A "radiological request" by which to conduct the radiological procedure may be influenced by the specific medical characteristics of the patient being examined. For instance, certain steps within the procedure may be altered, shortened, eliminated, or otherwise modified based upon patient characteristics and/or an anatomical structure to be examined.

The radiological procedure may involve the use of a radiological information system and be accomplished in accordance with an overall protocol. The protocol may have an associated work list consisting of the procedural steps to be performed. Each step may have a corresponding radiological "protocol item" to be employed during the course of the procedure.

A protocol item may be an instruction to medical personnel regarding the performance of a specific step in the procedure. For instance, the instruction may instruct the MTRA to inject a specific amount of a particular type of contrast agent at a certain point in the procedure.

A protocol item may be used to control a specific machine or "modality" during the procedure. For instance, the protocol items may be a set of physical parameters that control the operation of the modality. Modality as used herein may refer to a system consisting of one or more computers and medical hardware, such as coils, gradients, patient tables, C-arms, radiation sources and detectors, and/or other physical objects associated with acquiring internal images and producing image data for diagnosis. Other protocol items may be used.

An exemplary modality may be the fore-mentioned radiological imaging system. The system may include x-ray, MRI (magnetic resonance imaging), CT (computed tomography), ultrasound, PET (positron emission tomography), or other medical imaging devices. Accordingly, the protocol items may relate to physical parameters that determine the internal image acquired of a patient positioned within, on, or near an imaging device associated with the modality. The internal image may have associated image data.

The radiological procedure performed via the imaging system may be planned, at least partially, in advance with a software planning tool. The software planning tool may determine a number of the protocol items. A planning MTRA may use a RIS planning tool to manually select the radiological device to be used, the time of the procedure, and the work list. However, the planning MTRA may not have the expertise to select an appropriate protocol specifically tailored to account for the patient's characteristics. Additionally, there may be some "rules of thumb," guidelines, procedural steps, or other procedure techniques that the MTRA is not familiar with.

As the actual procedure may not be performed until sometime after an original procedure is initially planned, the actual procedure may be conducted by medical personnel other than the planning MTRA. To further complicate matters, the information required to select an appropriate protocol may not be available at the time the procedure is planned. For example, the requisite information may not have been provided by a transferring physician. Subsequent attempts to obtain the requisite information from the transferring physician or the patient directly may be ineffective, as they may be unavailable by telephone at the appropriate time. Expending time attempting to contact the previous physician and/or the patient is inefficient, and may create annoyance to everyone involved.

Accordingly, a database may be maintained that includes patient data. The patient data may detail patient specific information related to patient conditions, alerts, limitations, restrictions, and/or other characteristics. The patient data may be related to, or be collected, from the patient's medical history and/or file. Each patient characteristic may alter the appropriate selection and/or manner of performance of one or more procedural steps to achieve an optimum protocol. For example, based upon the patient information, a step may be altered, added, or omitted from the procedure. The "optimum" protocol may achieve approximately the best image quality and/or the lowest procedure time for a given set of patient characteristics. Other optimization goals may be used.

The patient data may be updated to reflect current, or relatively current, patient information. For example, the patient information is available from an archival system, such as a hospital patient database or a PACS. The patient's overall medical status and related conditions may change over time as the patient may develop new ailments, sicknesses, or diseases, or have certain operations performed. Hence, the database may be updated with current patient data from a remote medical facility either in real time or on a routine basis, such as with each patient visit to a medical facility. The up-to-date patient data may be gathered at one medical facility and transferred to a global database remotely accessible by other medical facilities interconnected via a communications network. Other data mining may be used to collect patient data, using either structured or unstructured data sources.

As a result, problems associated with inadequate patient information transfer between physicians, MTRAs, and/or medical facilities in general may be alleviated. With a MTRA having access to a network that includes a database with up-to-date patient information, inefficiencies and annoyances associated with contacting other medical personnel, such as previous physicians and MTRAs, as well as the patient directly, may be avoided.

In other words, a central or distributed database may be accessed by a number of remote medical facilities, such that if one medical facility has current information about the patient, medical personnel at all of the interconnected facilities may efficiently access the current patient data. In one embodiment, the database may be accessible via the DICOM (Digital Imaging and Communications in Medicine) standard. DICOM is a standard that permits different modalities to exchange data, such as patient data, procedure requests, images, and other medical data. The standard permits interoperability between different medical device/service vendors. As such, the standard may permit remotely, via a processor interconnected with a network, ordering from a vendor or otherwise accessing updated patient data and/or an optimum protocol tailored to account for patient characteristics and/or an anatomical structure to be examined. In other words, the optimum protocol may be defined within a radiological request generated at the vendor/service provider upon the request of a remote medical facility. Subsequently, the radiological request may be transmitted to or other wise remotely accessed from the remote medical facility via a network.

Each patient characteristic may alter which steps are included in a work list automatically suggested by a software planning tool, as well as the manner by which those steps are to be performed. As such, maintaining the patient database up-to-date facilitates automatically determining an appropriate work list based upon current patient conditions. For example, the planned radiological procedure, as defined by the radiological request, may result in the patient being exposed to radiation. If the patient becomes pregnant, steps may be altered or entirely omitted from the procedure to reduce the amount radiation exposure for the fetus. After child birth, the pregnancy limitation may no longer be a limitation on exposure. Alternatively, the exposure a patient is to receive may be limited based upon the anatomical structure to be examined or the age of the patient, as it may be preferable to limit the exposure that certain body areas (such as reproductive organs) or younger patients receive.

In addition to patient data, the database also may include procedural related data pertaining to various radiological procedures, as well as the steps to be performed during each procedure. The procedures may be related to examining or acquire images of a particular anatomical structure or body area of a patient. The procedures may be directed toward examining the head, torso, arms, legs, lungs, heart, stomach, hands, feet, liver, intestines, other organs, and/or other anatomical structures. The procedures may be related to a specific type of radiological device, such as x-ray, MRI, CT, PET, ultrasound, angiography, or other imaging devices. Data may be stored pertaining to additional, fewer, or alternate types of procedures.

The procedure related data may include protocol item data. The protocol item data may be associated with specific types of radiological procedures or individual work steps. The protocol items associated with a number of the steps in a given procedure may constitute an overall radiological "protocol." The protocol may provide an indication of the expected quality of the images to be acquired during the procedure, the anticipated time to complete the procedure, and/or the total amount of radiation that a patient or a particular anatomical structure will receive.

A processing unit may perform operations with the protocol items and patient data to generate a suggested work list that corresponds to a tailored protocol by which to conduct the procedure. The tailored protocol may provide an optimum procedure based upon the patient data. In other words, the protocol is tailored to minimize the impact of patient restrictions, limitations, or other medical conditions upon the performance and results of the procedure.

As a result, the quality of the images acquired may be enhanced, as well as the amount of radiation received and the time to complete the procedure may be reduced, for a given set of patient characteristics. Enhanced image quality facilitates diagnosis and early detection of illness as greater image detail provides a better understanding of the current status of the patient and may reveal diminutive problematic structures, such as developing lesions and tumors. Reduced procedure time may lower costs associated with each procedure.

The tailored protocol, as well as individual protocol items, may be automatically determined by a rule-based system or algorithm. The rule-based system may be a knowledge-based system comprising: (1) a database, (2) a set of rules, and (3) a control system with a rule interpreter, otherwise referred to as a "business rule engine." The tasks of the control system may include identifying suitable rules, employing the rules selected, and updating the database. In one embodiment, the rule-based algorithm may be integrated into the planning software of a radiological information system.

The database may include patient data that pertains to patient restrictions (so-called "medical alerts") in terms of the procedure, including those mentioned above. Medical alerts may include or related to (1) incompatibilities, such as contrast agent allergies, (2) artificial joints, (3) pacemakers, (4) pregnancy, (5) respiratory limitations or limited mobility, (6) age, (7) anamnesis or medical history, (8) admitting diagnosis (which may be based upon recently acquired patient data or images), and/or other conditions. Age may be a factor as the anatomy of a small child may be preferably examined differently from that of an adult. Depending upon the limitation, a different protocol for the procedure may be automatically selected, such that the procedure may be performed despite the limitation. As such, the database may contain protocols that are to be selected based upon the answers to various medical questions.

As an example of the effect that a medical alert may have upon the procedure, if the patient has difficulties breathing, a protocol may be selected that does not require the patient to hold his breath for a relatively long time (even if the procedure then takes longer overall and image quality suffers). Accordingly, the tailored protocol may factor in certain tradeoffs encountered to overcome a medical alert and still perform the procedure. As another example, for an MRI procedure of the head of an infant, a different protocol may be used as compared to the protocol used for a child over 6 months old.

The set of rules by which to automatically select a protocol may include an If-Then-Else routine and resemble the following format: IF . . . THEN . . . OTHERWISE (IF THEN ELSE). For instance, a rule may resemble: IF the stovetop is hot AND there is no pot on the stove THEN turn off the stove. More specifically, a general rule to select an appropriate protocol may be: IF "procedure=anatomical structure" AND "patient characteristic" THEN "use specific protocol." Hence, the logic rules may accept an anatomical structure to be examined and a patient characteristic as input to automatically select an appropriate protocol. The logic rules may be defined in code written in a programming language.

Another exemplary rule may be: IF "procedure=head" AND "age of the patient<6 months" THEN use protocol "\pediatric_head\program\zero to six months." The set of rules to be employed is not rigid, but rather the rule set may be adapted again and again. Thus, if new protocols are to be added later in time, then corresponding additional rules also may be defined. In one embodiment, the set of rules may be defined by the user. Other logic rules, algorithms, and routines may be used. For example, learned algorithms may be used.

The business rule engine may require certain preconditions be established. The preconditions may include (a) the planning MTRA has the patient data available, and (b) the business rule engine is integrated into the planning software of the RIS. In one embodiment, syngoMR™ software is employed and protocols may be named in a manner such that the intended use of the protocol is clear from the name, such as the program name above. Other software applications may be used.

A menu may group protocols by a corresponding anatomical structure to be examined or procedure to be performed. For instance, the menu may list groups of protocols by "shoulder," "elbow," "wrist," "hip," "knee," "ankle," "long-bone," "metastasis evaluation," "pediatric-head," and other groupings.

Each group of procedures listed may have a number of programs to be used, based upon patient characteristics. For instance, the pediatric-head programs may be classified by "standard," "zero to six months," "six months to one year," "seizure," "pituitary," "uncooperative," and/or "spectroscopy" qualifiers that identify different protocols related to examining the heads of small children. Based upon the patient characteristics, the rules employed may select an appropriate program from the available list. After which, a corresponding work list may be displayed on a screen. Additional, fewer, and alternate types of procedures and programs may be automatically selected.

The syngoMR™ or other software may be located only within MRI equipment, i.e., in the modality and not in the RIS where the procedure is planned. In one embodiment, the name of the protocol may be automatically linked via software with the procedure question being asked by the automated software solution to provide a suitable program suggestion.

Once the set of rules have been determined, a relationship between the patient characteristics and the optimum protocol for examining the patient may be automatically established. The business rule engine may adhere to the logic rules in a certain order and determine which rules may be used on the basis of patient characteristics detailed by the data. If a suitable rule has been found, a corresponding program may be executed. For example, an optimum protocol defined in the THEN part of a routine may be performed or presented automatically to the planning MTRA for review. As a result, automatically selecting a protocol for a radiological procedure may provide enhanced quality assurance.

Furthermore, for a given set of patient parameters, the automatic determination of a protocol may provide for standardization and replicability. Regardless of which MTRA does the planning, the same protocol may always be suggested. As a result, an optimum protocol may be employed more frequently.

Time savings and efficiency may result as well. Manual searches for an appropriate protocol may be avoided. Tracking down various physicians by telephone to inquire about the current status of a patient may be alleviated. With patients that have certain limitations, the procedure time may be shortened as unusable or undesirable measurements are avoided.

Moreover, the embodiments discussed herein may enhance patient safety. With patients that have metal implants, such as an artificial hip joint, the image quality may be affected, and incorrect diagnoses may ensue. However, the examining MTRA may be given a warning or other indication that a potential problem may exist before the procedure is commenced, providing the MTRA with the opportunity to change problematic protocol items.

In one embodiment, the rule-based engine may adapt the radiological procedure to account for user preferences. As a user makes various decisions, a processor may store data defining the previous decisions made. For instance, in a situation in which the system does yield a unique radiological procedure based upon patient characteristics, the system may store data associated with the procedure that the user performed. For subsequent, procedures in which no unique steps are determined based upon patient characteristics, the system may present the radiological procedure previously used to the user for consideration.

I. Exemplary Method

FIG. 1 illustrates an exemplary method of planning a radiological procedure 100. The method 100 may include generating and maintaining a database 102, determining a set of rules 104, and automatically selecting a procedure 106. The method may include additional, fewer, or alternate actions.

Figure 2:
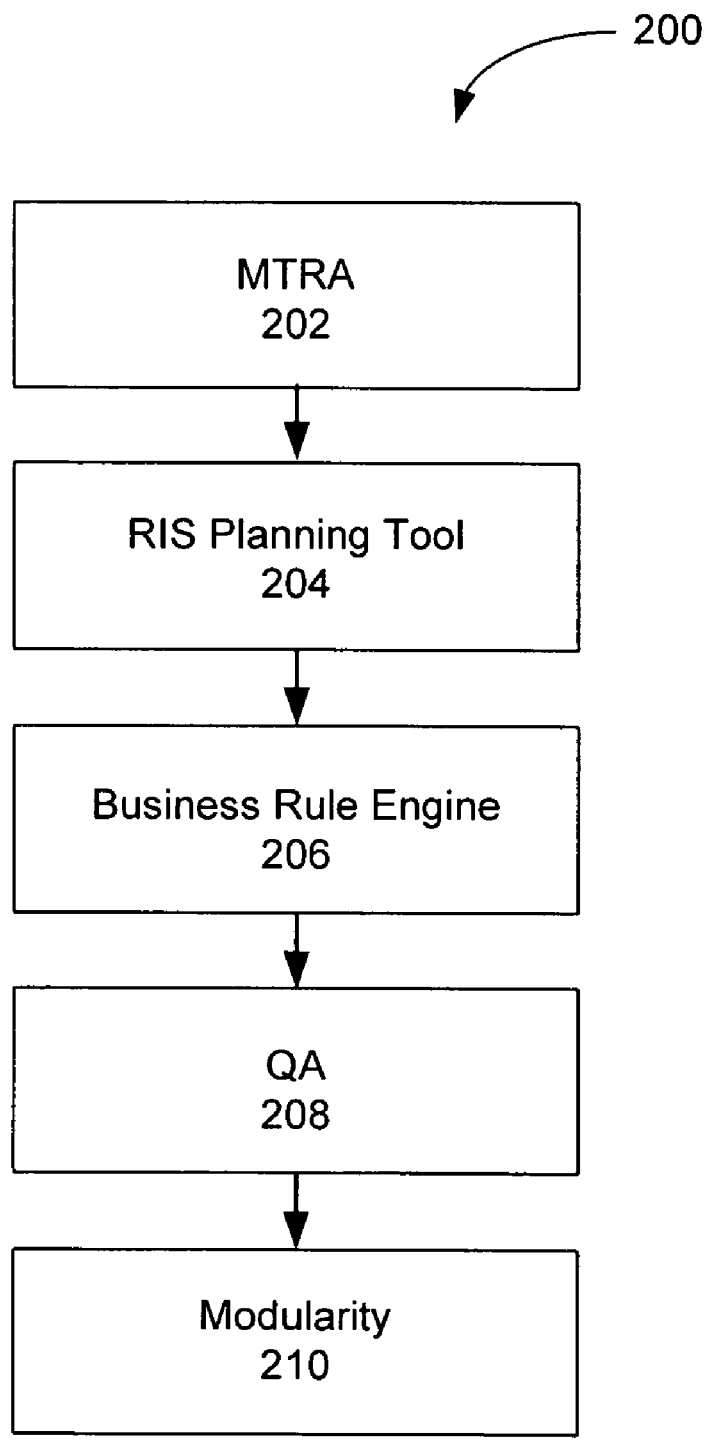
FIG. 2 illustrates an exemplary application of the method of planning a radiological procedure.

The method 100 may include generating and maintaining a database 102. The database maintained may include protocol items and patient data as discussed herein. The data may be gathered automatically from various interconnected medical facilities and/or via manual data input, which may be required to update the data. Additionally, FIG. 2 illustrates an exemplary application of the method of planning a radiological procedure 200. The method may be practiced by a MTRA 202 or other medical personnel. The MTRA 202 may use a radiology information system ("RIS") 204 to facilitate planning the radiological procedure.

The RIS planning tool 204 may determine a number of the protocol items. The RIS may utilize a software component with which protocols may be administered. In one embodiment, the software component is File Explorer in Windows XP™. Other software components may be used.

The method 100 may include determining a set of rules 104. A rule-based system may facilitate the planning of the radiological procedure, as described above. With the exemplary application of the method shown in FIG. 2, the set of rules may be employed by a business rule engine 206. The business rule engine may include one or more algorithms to determine particular protocol items to employ based upon patient characteristics. The algorithms may be implemented via software and/or hardware. Protocol items associated with the physical operation and positioning of various imaging devices may be pre-determined and stored in the database.

Figure 3:
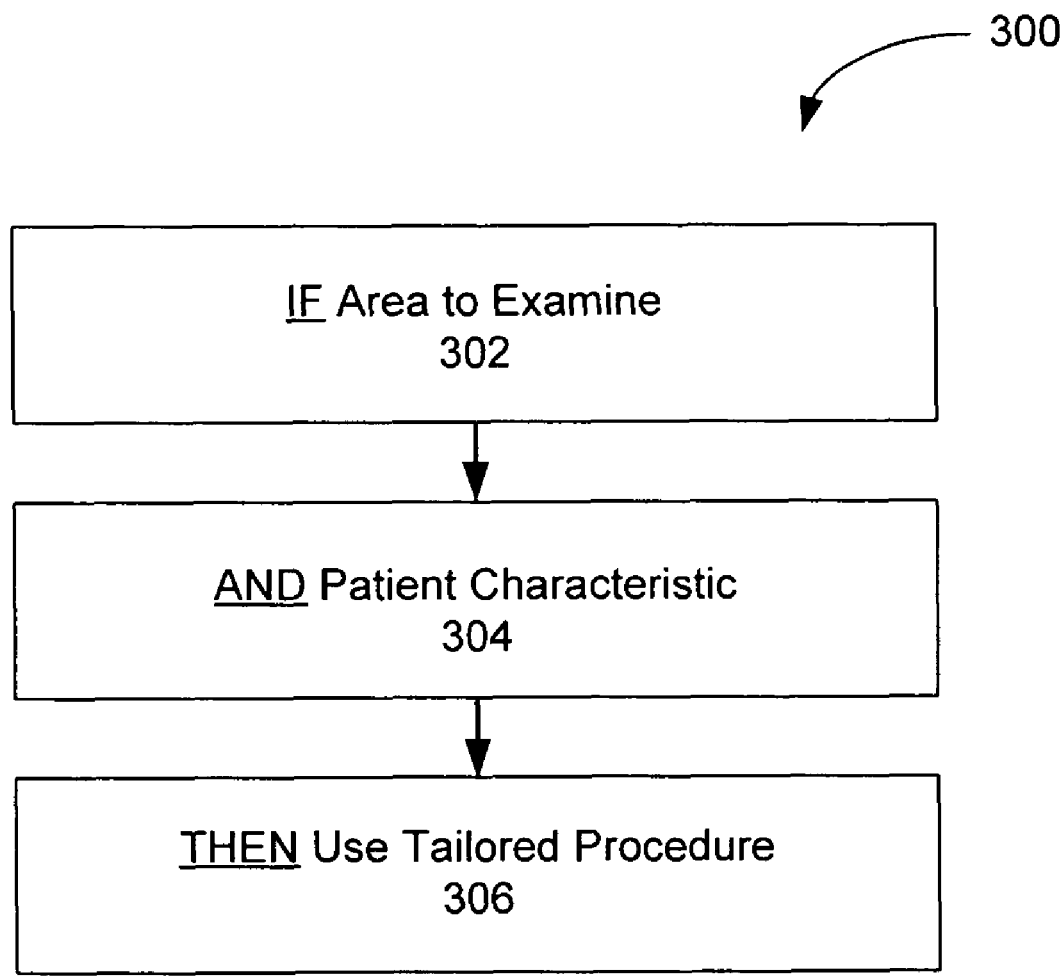
FIG. 3 illustrates an exemplary decision rule.

FIG. 3 illustrates an exemplary decision rule 300. The decision rule 300 may include the use of an If-Then-Else or other routine. The rule 300 may accept the area to be examined 302 and a patient characteristic 304 as inputs to determine a tailored procedure 306. Other decision rules may be used. For instance, nested loops, nested if-then loops, while statements, call statements, decision trees, binary trees, or other decision matrixes may be used. In one embodiment, the decision rule is programmed in the C++ programming language. Other programming languages may be used.

The method 100 may include automatically selecting a procedure 106. For the automatic selection of the optimum protocol, a search operation may be triggered, such as via a button on a user interface, which may call up the business rule engine of the rule-based system operable to accept patient data as an input parameter. The patient data may include a patient identifier that identifies the patient to which the data belongs.

As illustrated in FIG. 2, the MTRA may perform quality assurance 208 by reviewing the protocol suggested by the business rule engine 206. After the MTRA ensures that the protocol is appropriately tailored to satisfy the patient characteristics, the protocol may be performed via the corresponding modularity 210 or other workstation. Operating the modularity 210 in accordance with the suggested protocol may result in optimum or enhanced quality internal images of the patient being acquired via the modularity 210 for the given patient characteristics.

In one embodiment, the RIS planning tool may employ a bitmap display, such as an information screen displayed within a graphical user interface (GUI). The bitmap may be generated based upon the data used to determine the protocol. The data may be received from a remote location, a local database, or entered by a user. The data may include patient data, such as name, age, weight, and other characteristics, as well as the type of procedure, such as a procedure of the head or torso. The data may include a type of alert, such as age<6 months. The data may be collected at one location and then forwarded to a planning tool.

The planning tool may generate a protocol based upon the data. The protocol may then be stored in a database. After which, the protocol may be (remotely) accessed via request. For instance, the protocol may be accessed via a terminal adapted to conform to the DICOM standard. The terminal may be dedicated to the radiological device or system that will employ the protocol.

In another embodiment, the RIS planning tool may use Microsoft Office Visio™ or other program to display information on a screen. The RIS planning tool may use alternate types of software programs to present the protocol tailored to satisfy patient conditions to the user.

II. Exemplary Data Processor

Figure 4:
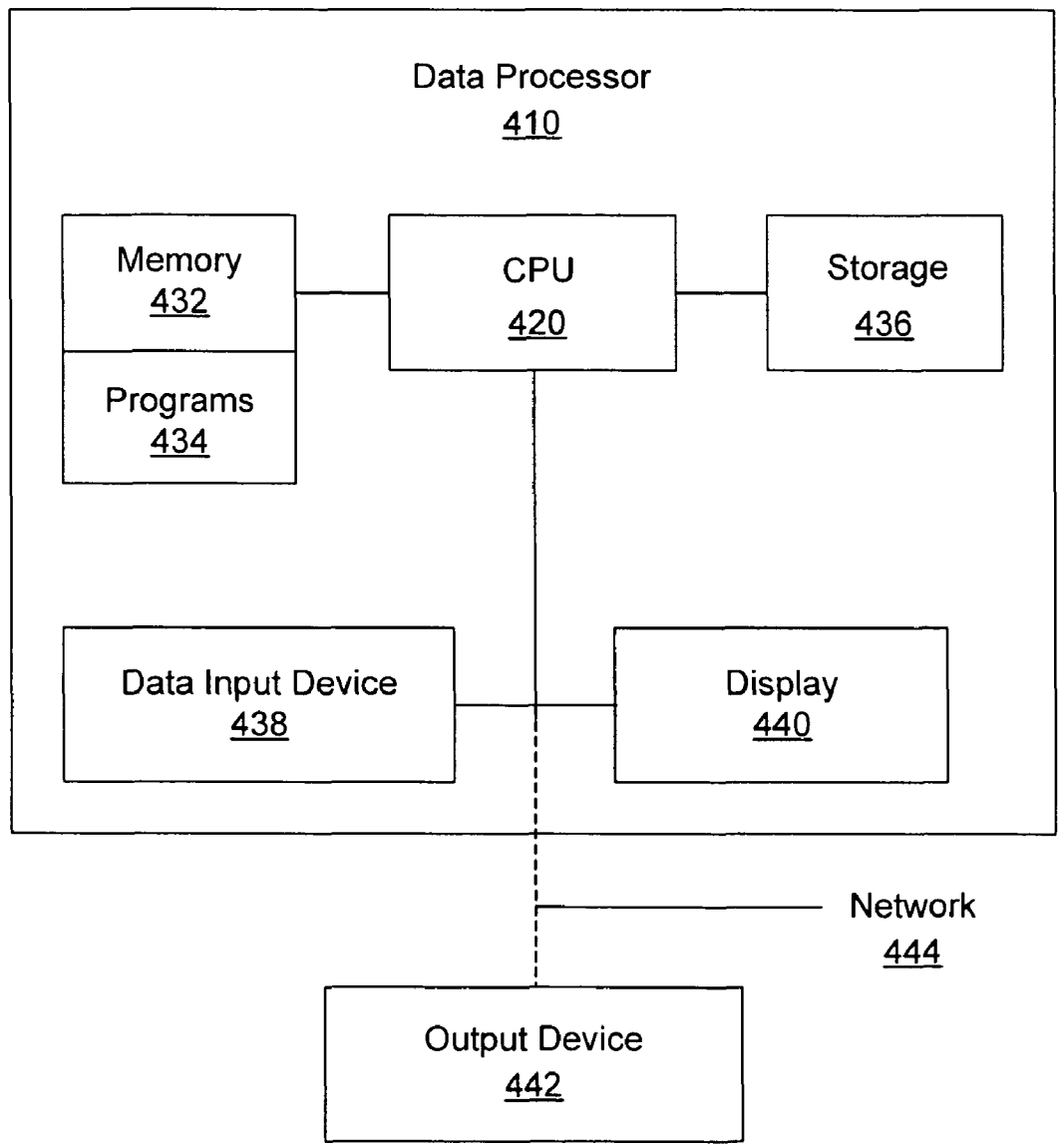
FIG. 4 illustrates an exemplary data processing system operable to plan a radiological procedure.

The method for planning a radiological procedure may be facilitated by a data processing system. FIG. 4 is a block diagram of an exemplary data processor 410 configured or adapted to provide functionality for planning medical procedures. The data processor 410 may include a central processing unit (CPU) 420, a memory 432, a storage device 436, a data input device 438, and a display 440. The data processor 410 also may have an external output device 442, which may be a display, a monitor, a printer or a communications port. The data processor 410 may be a personal computer, work station, server, imaging system, or other system. The data processor 410 may be interconnected to a network 444, such as an intranet, the Internet, or an intranet connected to the Internet. The data processor 410 may be interconnected to another location via the network 444 either by data lines or by wireless communication. The data processor 410 is provided for descriptive purposes and is not intended to limit the scope of the present system. The data processor may have additional, fewer, or alternate components.

A program 434 may reside on the memory 432, storage device 436, or another memory (e.g., hard drive removable media, RAM, or network buffer). The program 434 may include one or more sequences of executable code or coded instructions that are executed by the CPU 420. The program 434 may be loaded into the memory 432 from the storage device 436 or network or removable media. The CPU 420 may execute one or more sequences of instructions of the program 434 to process data. The program 434 may provide functionality as discussed herein.

Patient and protocol item data may be entered via the data input device 438 or another input device, or received via the network 444 or other network. The data processor 410 may receive and store patient and protocol item data received in the memory 432, the storage device 436, or other storage unit. The program 434 may direct that the data received be stored on or read from machine-readable medium, including secondary storage devices such as hard disks, floppy disks, CD-ROMS, and DVDs; electromagnetic signals; or other forms of machine readable medium, either currently known or later developed.

The program 434 may instruct the data processor 410 to depict the patient and/or protocol item related information in one or more windows on the display 440, the external output device 442, or other display screen. The patient and/or protocol item related information may be depicted visually or textually. The data processor 410 may retrieve the patient and/or protocol item data from machine-readable medium, including secondary storage devices such as hard disks, floppy disks, CD-ROMS, and DVDs; electromagnetic signals; or other forms of machine readable medium, either currently known or later developed.

The program 434 may direct the data processor 410 to scroll through a visual or textual depiction of patient and/or protocol item related information, such a medical file history or a work list. The data processor 410 may divide the display 440, output device 442, or other display screen into multiple virtual sub-regions. Each of the virtual sub-regions may be associated with a specific patient and/or protocol items. For instance, the display may be split into four quadrants. Each quadrant may be dedicated to a specific step in the procedure. Other sub-regions may be provided.

The data processor 410 may cause display of patient and/or protocol item information on the display 440, output device 442, or other display screen. The patient data may correspond to patient characteristics and medical alerts. The protocol item data may be associated with steps to be performed during a medical procedure. The data processor 410 also may display icons on the display 440, output device 442, or other display screen. The display 440, output device 442, or other display screen may be a touch screen, a touch pad, a haptic device, or other vibrational or physical feedback device.

The user interface may accept one or more operations performed on the display and/or icons to reveal further information. For instance, the user interface may provide for the selection and display of a dedicated procedural step page after the user clicks upon a step related icon. The dedicated step page may present further textual or graphical information related to the performance of the step. The user interface also may present further textual or graphical information related to a specific patient or procedure step after user selection. Other operations may be performed The data processor 410 may cause generation of various icons on the display 440, output device 442, or other display screen. A user interface may accept one or more operations performed upon the icons. For example, the user may select an icon associated with ordering a tailored protocol from a remote location.

While the invention has been described above by reference to various embodiments, it should be understood that many changes and modifications can be made without departing from the scope of the invention. The description and illustrations are by way of example only. Many more embodiments and implementations are possible within the scope of this invention and will be apparent to those of ordinary skill in the art. The various embodiments are not limited to the described environments and have a wide variety of applications.

It is intended in the appended claims to cover all such changes and modifications which fall within the true spirit and scope of the invention. Therefore, the invention is not limited to the specific details, representative embodiments, and illustrated examples in this description. Accordingly, the invention is not to be restricted except in light as necessitated by the accompanying claims and their equivalents.

The invention claimed is:

1. A data processing system for planning radiological requests, the system comprising:
   a memory configured to store patient data associated with a patient that is to undergo a current radiological procedure and a plurality of pre-determined protocol items related to acquiring images of one body area of the patient, each of the pre-determined protocol items being associated with the physical operation of a medical imaging device during a radiological procedure;
   a processor configured to retrieve updated patient data from a remote medical facility and update the patient data stored in the memory to reflect the updated patient data retrieved from the remote medical facility, the updated patient data being acquired during a previous examination of the patient performed at the remote medical facility and containing a new patient restriction identified during the previous examination; and
   the processor further configured to determine an optimized protocol by which to conduct the current radiological procedure by employing a rule-based algorithm acting upon the updated patient data, wherein the rule-based algorithm employed automatically determines the optimized protocol from among the plurality of pre-determined protocol items related to acquiring images of one body area of the patient as a function of (1) a body area of the patient to be examined during the current radiological procedure and (2) the new patient restriction contained within the updated patient data retrieved from the remote medical facility, and the processor facilitates the performance of the optimized protocol to acquire images of the body area of the patient to be examined such that the new patient restriction identified during the previous examination of the patient performed at the remote medical facility is automatically accounted for during the current radiological procedure.

2. The system of claim 1, wherein the processor is operable to control an imaging device to conduct the current radiological procedure in accordance with the optimized protocol.

3. The system of claim 2, wherein the optimized protocol results in an optimum image quality in the images acquired by the imaging device in view of (1) the body area to be examined and (2) the new patient restriction identified during the previous examination of the patient.

4. The system of claim 2, wherein the imaging device is a modality.

5. The system of claim 2, wherein the optimized protocol results in an optimum procedural time required to acquire images of the body area to be examined and account for the new patient restriction identified during the previous examination of the patient.

6. A data processing system for planning radiological requests, the system comprising:
   a memory storing a plurality of pre-determined protocols associated with a specific type of radiological device operable to acquire images of a body area of a patient;
   a processor configured to retrieve up-to-date patient characteristic information associated with the patient from a remote database, the up-to-date patient characteristic information being acquired during a previous medical examination of the patient performed at a remote medical facility; and
   the processor further configured to employ a rule-based algorithm to select an optimized protocol by which to conduct a radiological procedure from among the plurality of pre-determined protocols associated with the specific type of radiological device, wherein the up-to-date patient characteristic information includes a new patient restriction identified during the previous medical examination of the patient performed at the remote medical facility, and the rule-based algorithm selects the optimized protocol from among the plurality of pre-determined protocols associated with the specific type of radiological device as being a function of (1) the new patient restriction identified during the previous medical examination of the patient performed at the remote medical facility and (2) the body area of the patient to be examined, and the optimized protocol selected by the rule-based algorithm from among the plurality of pre-determined protocols associated with the specific type of radiological device is used by the processor in acquiring images of body area of the patient to be examined such that the new patient restriction identified during the previous medical examination of the patient performed at the remote facility is accounted for in the acquiring of the images.

7. The system of claim 6, wherein the optimized protocol comprises a list of protocol items to be employed during the course of the radiological procedure.

8. A method of planning a radiological request, the method comprising:

pre-determining a plurality of potential procedural steps associated with an overall radiological procedure performed via an imaging device to acquire medical images of a patient;

storing the pre-determined plurality of potential procedural steps in a database;

retrieving a new patient restriction that impacts the overall radiological procedure performed via the imaging device from a remote medical facility via a processor, the new patient restriction being identified during a previous examination of the patient performed at the remote medical facility;

automatically tailoring the overall radiological procedure to account for the new patient restriction identified by configuring the processor to accept the new patient restriction identified during the previous examination of the patient performed at the remote medical facility as a first input parameter and a body area of the patient to be examined as a second input parameter, and then automatically select one or more procedural steps from among the pre-determined plurality of potential procedural steps associated with the overall radiological procedure, as a function of the first and second input parameters, to achieve an optimized protocol that is optimum for the new patient restriction identified and the body area of the patient to be examined; and acquiring images of the body area of the patient using the optimized protocol.

9. The method of claim 8, wherein the optimized protocol comprises a list of protocol items to be employed during the overall radiological procedure.

10. A method of planning a radiological request, the method comprising:

retrieving updated patient information from a database, the updated patient information including a new patient restriction identified during a previous medical examination of a patient performed at a remote medical facility;

identifying a body area of the patient to be examined;

a rule-based algorithm automatically selecting, from a plurality of pre-determined protocol items associated with the body area, a protocol item to be employed during a radiological procedure via a processor as a function of the new patient restriction identified during the previous medical examination of the patient performed at the remote medical facility and the body area of the patient to be examined; and acquiring images of the anatomical structure body area of the patient to be examined via an imaging device controlled by the processor in accordance with the protocol item automatically selected.

11. The method of claim 10, wherein the protocol item automatically selected comprises a set of physical parameters that control the acquisition of the image by the imaging device.

* * * * *

UNITED STATES PATENT AND TRADEMARK OFFICE
CERTIFICATE OF CORRECTION

PATENT NO. : 7,885,828 B2  
APPLICATION NO. : 11/654415  
DATED : February 8, 2011  
INVENTOR(S) : Karlheinz Glaser-Seidnitzer et al.

Page 1 of 1

It is certified that error appears in the above-identified patent and that said Letters Patent is hereby corrected as shown below:

In the claims:

Column 12, claim 10, line 32, please delete "anatomical structure" before "body area."

Signed and Sealed this
Twenty-fourth Day of September, 2013

Teresa Stanek Rea
*Deputy Director of the United States Patent and Trademark Office*